United States Patent [19]
Kirk et al.

[11] Patent Number: 4,986,076
[45] Date of Patent: Jan. 22, 1991

[54] ISOTHERMAL COOLING METHOD AND DEVICE

[75] Inventors: Kenneth Kirk, 27 Ancaster Ct., Dartmouth, Nova Scotia, Canada, B2V 1J2; Cassius D. Remick, Waterloo, Canada; Charles M. Burns; Berthold H. Habicher, both of Kitchener, Canada

[73] Assignee: Kenneth Kirk, Dartmouth, Canada

[21] Appl. No.: 398,936

[22] Filed: Aug. 28, 1989

[51] Int. Cl.⁵ ............................................. F25D 5/00
[52] U.S. Cl. ................................. 62/4; 62/294; 62/480; 62/530
[58] Field of Search .................... 62/4, 294, 480, 530; 206/219

[56] References Cited

U.S. PATENT DOCUMENTS

| | | | |
|---|---|---|---|
| 2,882,692 | 4/1959 | Robbins | 62/4 |
| 2,898,744 | 8/1959 | Robbins | 62/4 |
| 2,907,173 | 10/1959 | Robbins | 62/4 |
| 3,095,291 | 6/1963 | Robbins | 62/4 |
| 3,149,943 | 9/1964 | Amador | 62/4 |
| 3,429,315 | 2/1969 | McDonald | 62/4 X |
| 3,887,346 | 6/1975 | Erdman | 62/4 |
| 3,893,834 | 7/1975 | Armstrong | 62/4 |
| 3,950,158 | 4/1976 | Gossett | 62/4 |
| 4,049,408 | 9/1977 | Patel | 62/4 |
| 4,427,010 | 1/1984 | Marx | 62/4 X |
| 4,522,640 | 6/1985 | Jagoe | 62/4 |
| 4,723,974 | 2/1988 | Ammerman | 62/4 |
| 4,780,117 | 10/1988 | Lahey | 62/4 |
| 4,903,493 | 2/1990 | Van Iperen et al. | 62/4 X |

Primary Examiner—Lloyd L. King
Attorney, Agent, or Firm—Carson, Armstrong

[57] ABSTRACT

One version of the invention provides a method for cooling and maintaining an object at a substantially constant temperature. The method includes adding a salt that dissolves endothermically in water to a mixture containing at least water, a surfactant and an emulsified thermal buffer. The "salt:water:thermal buffer" ratio is such that the reaction provides sufficient endotherm to cool the system to the freezing point of the thermal buffer and effect at least a partial phase change of the thermal buffer. Another version of the invention provides a device for effecting the method. The device has a reaction compartment consisting of two portions separated by a frangible barrier, one portion containing the emulsified thermal buffer in water and the other portion the salt that dissolves endothermically into solution. One specific version of the device is a container for transporting an amputated extremity such as a severed finger to another location for replantation.

13 Claims, 2 Drawing Sheets

ISOTHERMAL COOLING METHOD AND DEVICE

BACKGROUND OF THE INVENTION

1. Field of the Invention

This invention relates to cooling devices and methods that use endothermic chemical and/or physical reactions to provide a heat sink. As a particular application, it relates to cooling methods and devices for injured body parts or severed extremities.

2. Description of the Prior Art

Various types of devices that use endothermic reactions for cooling purposes are known. For example, U.S. Pat. Nos. 3,095,291 and 2,898,744 granted to Robbins disclose respectively a "COOLING ENVELOPE WITH BREAKABLE DIAPHRAGM" and a "CHEMICAL FREEZING PACKAGE". U.S. Pat. No. 3,429,315 granted to McDonald discloses a "CHEMICAL REFRIGERANT BLANKET". U.S. Pat. 4,049,408 granted to Patel for a "DISPOSABLE COLD PACK FOR BLOOD SPECIMEN" is of particular interest because it discloses a device that maintains a blood sample at a temperature of 28 to 40 degrees Fahrenheit with no risk of subcooling below the critical lower temperature.

Devices designed specifically for cooling severed body parts are also known. Examples of such devices are described and illustrated in U.S. Pat. No. 4,723,974 dated Feb. 9, 1988 and granted to Ammerman for a "TRANSPORTING CONTAINER FOR AN AMPUTATED EXTREMITY".

Ammerman discloses a container consisting of an inner compartment surrounded by an exterior compartment. The exterior compartment is divided into two portions by a frangible separating barrier. One portion contains one part of a cooling medium such as water. The other portion contains another part of the cooling medium such as ammonium nitrate. Physical deformation of the flexible container breaks the frangible barrier and thus results in mixing together of the contents of the two portions.

Ammerman also discloses a container having a plurality of cooling bags in the exterior compartment each separated into two portions by a frangible barrier. Instructions are provided to the user of the container specifying when to break the barriers to maintain adequate cooling. Also disclosed is essentially the same device with a plurality of portions in each cooling bag. This design prevents the accumulation of granulated ammonium nitrate into one particular location and thus helps to effect a more even distribution of the cooling effect across the container assembly. In particular, an objective of this design was to prevent "hot spots" in which certain areas of the inner compartment would not be adequately cooled.

German Offenlegungsschrift No. 23 05 504 discloses a cooling bag that includes a chemical used as a thermal buffer.

SUMMARY OF THE INVENTION

It is an object of the invention to overcome some of the disadvantages and inconveniences of the prior art.

The present invention, in a first aspect, contemplates the provision of a method for cooling and maintaining an object at a substantially constant temperature. A salt that dissolves endothermically in water is added to a mixture containing at least water, a surfactant and an emulsified thermal buffer. The "salt:water:thermal buffer" ratio is such that the reaction provides sufficient endotherm to cool the system to the freezing point of the thermal buffer and effect at least a partial phase change of the thermal buffer. The object may be brought into direct contact with the resulting mixture by immersing it in the mixture. Alternatively, the mixture may be contained within a reaction compartment and the object may be brought into indirect contact with the mixture by placing the object adjacent to the reaction compartment. The use of an emulsified thermal buffer is a key feature of the method and its importance is related to heat transfer considerations.

In a second aspect, the invention contemplates the provision of a device for effecting the method described above. The device consists of a reaction compartment consisting of two portions separated by a frangible barrier, one portion containing an emulsified thermal buffer in water and the other portion a salt that dissolves endothermically into solution. The device is activated by breaking the frangible barrier in the reaction compartment and allowing the endothermic reaction to proceed. In principle, the temperature of the reaction compartment and its contents drops until it reaches the "freezing point" of the thermal buffer. The heat absorbed by the endothermic reaction is subsequently substantially taken from the emulsified thermal buffer which consequently undergoes a phase change. The reaction proceeds until most of the thermal buffer has been frozen. Cooling of the object is achieved by bringing the object into contact with the reaction compartment. Heat transferred from the object is absorbed by the heat of fusion of the thermal buffer. As long as the buffer is in a two phase state its temperature will remain at its melting point. Instead of a gradual increase in the temperature of the object with time, a substantially constant temperature is maintained over a protracted period of time.

In another aspect of the invention, the reaction compartment and the object are contained within an insulating outer shell. One particular embodiment of the invention consists of a container for transporting an amputated extremity such as a severed finger to a location for replantation. The device cools the severed finger to a target temperature and maintains the finger very close to that temperature for a protracted period of time despite variable ambient temperatures.

In yet another aspect of the invention, more than one salt is used in order to minimize the mass of reactants needed to produce the required endotherm. The different salts may be kept in separate portions of the reaction compartment to prevent reaction of the dry salts prior to activation of the device.

Further features of the invention will be described or will become apparent in the course of the following detailed description.

BRIEF DESCRIPTION OF THE DRAWINGS

In order that the invention may be more clearly understood, the preferred embodiment thereof will now be described in detail by way of example, with reference to the accompanying drawings, in which.

DETAILED DESCRIPTION OF THE PREFERRED EMBODIMENT

Figure 1:
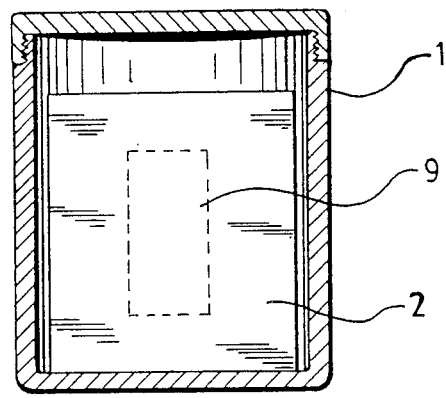
FIG. 1 is an elevation view of the preferred embodiment of the invention with the insulating exterior shell shown in section.
Figure 2:
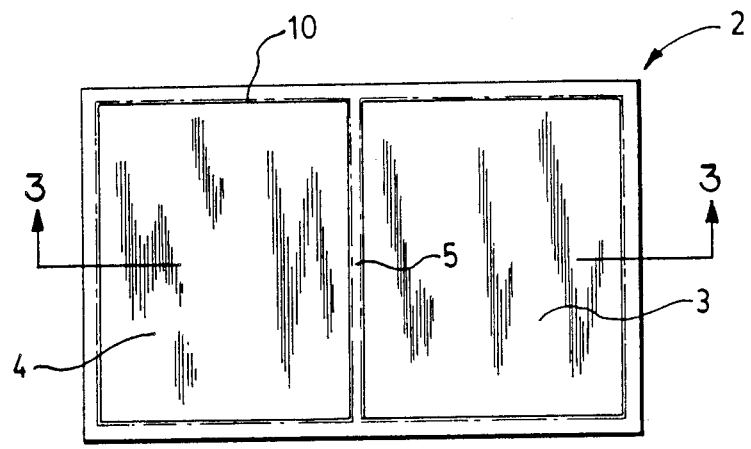
FIG. 2 is a plan view of the reaction chamber, in this case, a cooling bag.
Figure 3:
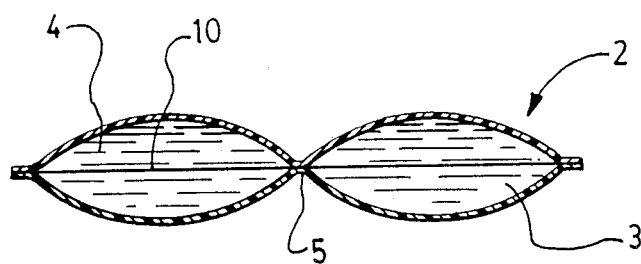
FIG. 3 is a vertical cross-sectional view taken along the line 3—3 of FIG. 2.

The test apparatus consists of an insulating outer shell such as a vacuum flask 1 and a reaction compartment, more specifically, at least one flexible, plastic cooling bag 2 wrapped around a "water finger" 9 (described below). The plastic cooling bag 2 is sealed at edges 10, for example, by heat sealing. The cooling bag 2 is separated by a frangible barrier 5 into a salt portion 3 and a liquid portion 4.

An emulsion is prepared by dissolving a surfactant in water and slowly adding a thermal buffer with vigorous stirring. A salt is weighed into the salt portion 3 of the cooling bag 2 and the aqueous emulsion is poured into the liquid portion 4.

The test apparatus is activated by squeezing a cooling bag 2 and thereby rupturing the frangible barrier 5. Preferably, the rupturing is performed on an expanded polystyrene ("Styrofoam", trade mark) pad in order to reduce heat transfer from the surroundings into the cooling bag 2. The cooling bag 2 is shaken, nested together around a severed human finger, inserted into the vacuum flask 1 and the vacuum flask 1 is capped.

The test apparatus was tested in the laboratory. The reagents used in the test were the salt, potassium thiocyanate (KSCN), and de-ionized water. The surfactant used was octylphenol ethoxylate sold under the trade name Triton X-100. The thermal buffer was cyclohexane ($C_6H_{12}$).

Two tests included a "water finger" 9 to simulate a severed human finger. The water finger 9 was made from a polyethylene bag 35 mm by 150 mm weighing 1.35 g. The sealed water finger was approximately 25 mm in diameter and filled to a depth of 100 mm with 40.20 g water, the remainder of the bag being filled with air.

At the start of the tests, a thermocouple was taped to the water finger 9 or to the cooling bag 2 if no water finger 9 was used. The frangible barrier 5 was completely ruptured and the contents mixed by grasping the ends of the cooling bag 2 and shaking with a vigorous side-to-side motion for one minute. In some of the tests, the frangible barriers were ruptured on the polystyrene pad. As described above, the cooling bag 2 was folded along its long axis, nested around the water finger 9 or if no water finger 9 was used around the thermocouple, inserted into the vacuum flask 1 and capped. The vacuum flask 1 was shaken axially for ten seconds per minute for the first five minutes of each test. The temperature was recorded using a strip chart recorder. The test continued until the cooling bag 2/water finger 9 temperature exceeded 10 degrees Celsius.

The results of the tests are summarized in Table 1:

TABLE 1

| Test Apparatus Experimental Results | | | | | |
|---|---|---|---|---|---|
| Exp. # | 1 | 2 | 3 | 4 | 5 |
| KSCN (g) | 199.11 | 198.14 | 260.30 | 249.51 | 249.39 |
| H₂O (g) | 100.07 | 102.2 | 130.90 | 125.23 | 125.13 |
| Triton X-100 (g) | 1.05 | 1.04 | 1.34 | 1.17 | 1.25 |

TABLE 1-continued

| Test Apparatus Experimental Results | | | | | |
|---|---|---|---|---|---|
| cyclohexane (g) | 287.95 | 290.16 | 391.89 | 375.23 | 374.35 |
| pouch water | 0.00 | 17.08 | 15.91 | 16.27 | 15.77 |
| finger | no | no | no | yes | yes |
| pad | no | no | yes | yes | yes |

| Time (hrs.) | Temperature (degrees C.) | | | | |
|---|---|---|---|---|---|
| 0 | 23 | 23 | 23 | 23 | 23 |
| 0.2 | 6.5 | 23 | 7.0 | 23 | 8.0 |
| 0.4 | 6.5 | 23 | 7.0 | 8.0 | 8.0 |
| 1.0 | 6.5 | 7.5 | 7.0 | 8.0 | 7.8 |
| 2.0 | 6.5 | 8.2 | 7.0 | 8.0 | 7.8 |
| 3.0 | 6.5 | 8.5 | 7.0 | 8.0 | 7.8 |
| 4.0 | 7.0 | 9.0 | 7.0 | 8.0 | 7.8 |
| 4.5 | 7.0 | 9.0 | 7.2 | 8.0 | 7.8 |
| 5.0 | 7.7 | 9.4 | 7.2 | 8.0 | 7.8 |
| 5.5 | 7.7 | 9.4 | 7.5 | 8.0 | 7.8 |
| 6.0 | 8.5 | 9.4 | 8.0 | 8.4 | 8.4 |
| 7.0 | 9.1 | | 8.4 | 8.6 | 8.4 |
| 8.0 | 9.6 | | 8.4 | 9.4 | 9.0 |
| 9.0 | 9.6 | | 9.4 | 10 | 9.6 |
| 10.0 | | | 9.7 | | 9.6 |
| 11.0 | | | 9.7 | | 10 |

Note:
In experiment 1, a temperature of 10 degrees was reached at 9.1 hours; in experiment 2, it was reached at 6.2 hours; in experiment 3, it was reached at 11.2 hours.

In experiment #2 of Table 1 the cooling bag 2 was ruptured directly on the bench top rather than on the expanded polystyrene pad. This test had the shortest cooling duration. Experiments 4 and 5 are essentially replicates showing the reproducibility of these test results.

An important feature of the test apparatus is the use of an emulsified thermal buffer. As mentioned earlier, German Offenlegungsschrift No. 23 05 504 discloses a cooling bag that includes a chemical used as a thermal buffer. Apparently, the thermal buffer is contained in a plastic pouch that is sandwiched between the object to be cooled and the reaction compartment. It appears that the thermal buffer is not emulsified.

It is very important for heat transfer reasons that, at the target temperature of the device described above, the thermal buffer be in a substantially uniform two phase ("slush") state and have a high rate of heat transfer. These characteristics help maintain a uniform temperature in the plastic pouch and hence help maintain the object with which it is brought into contact at that same target temperature. In addition, it is possible that non-uniform freezing of the thermal buffer will result in the creation of a barrier to heat transfer. For example, from experimental results it can be predicted that if cyclohexane were used in the plastic pouch of the German device, the cyclohexane that is immediately adjacent to the reaction compartment would freeze to form a solid with the consistency of amorphous wax and with a poor rate of heat transfer. An insulating barrier to further heat transfer from the cyclohexane and the object into the reaction compartment would thus be created. An alternate thermal buffer that can be maintained in the uniform slush state at its melting point would have to be identified in order to make best use of the German device.

Cyclohexane is thus not a practical thermal buffer unless it is emulsified as is taught by the present invention. Emulsification ensures that a slush-like state is created even though the properties of the thermal buffer are such that in its pure state at the target temperature a uniform two-phase buffer does not exist. Emulsification also improves heat transfer between the thermal buffer and the reactants. It allows for the option of eliminating the separate thermal buffer pouch used in the German device. The elimination of the pouch walls between the thermal buffer and the reactants improves heat transfer.

Figure 4:
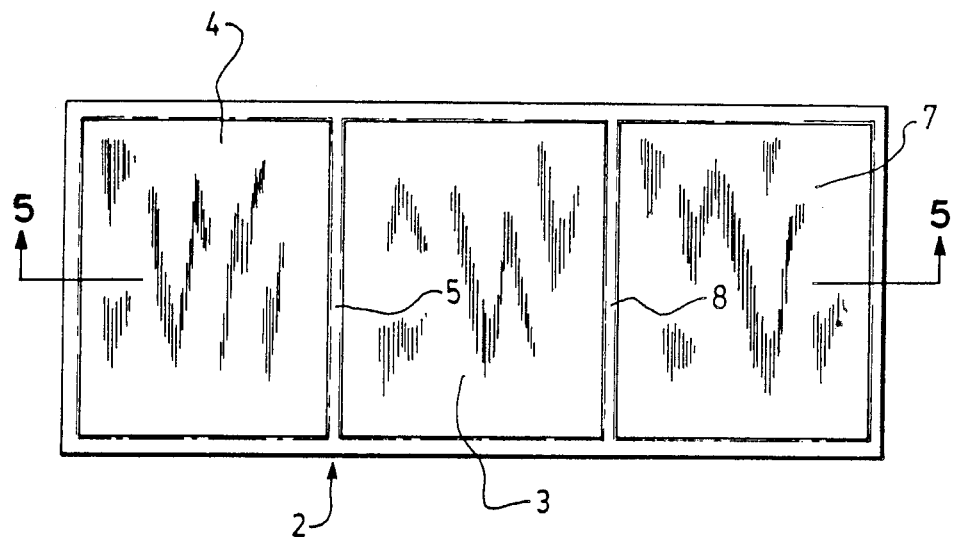
FIG. 4 is a plan view of an alternate embodiment of the invention.
Figure 5:
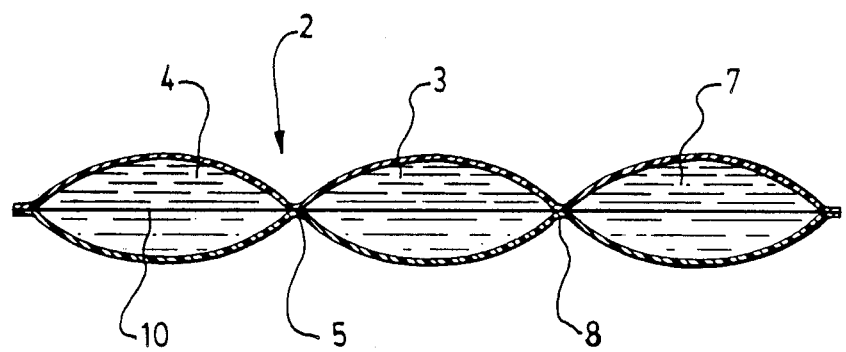
FIG. 5 is a vertical cross-sectional view taken along the line 5—5 of FIG. 4.

FIG. 4 illustrates a possible alternate embodiment of the invention which might be somewhat similar to the German device. The reaction compartment, in this case, the cooling bag 2, includes as in the first embodiment the salt portion 3 and the liquid portion 4 separated by the frangible barrier 5. Adjacent to and integral with the salt portion 3 is a thermal buffer compartment such as the buffer portion 7. The buffer portion 7 is essentially identical to the other two portions of the invention. The edge 8 of the cooling bag 2 is, of course, not frangible.

Some of the inconveniences of the German device could possibly be overcome by using the embodiment illustrated in FIG. 4, although such an embodiment has not actually been tested. The salt is inserted into the salt portion 3, water is inserted into the liquid portion 4 and the aqueous emulsion is inserted into the buffer portion 7. This embodiment is used in a mode substantially identical to that of the preferred embodiment.

For the test apparatus and for any given embodiment of the invention the reagent quantities are very important. Without prior calculations and experimentation it was not possible to assert that a device such as the test apparatus was practicable. For example, the optimal quantities of reagents required in order to meet minimal design criteria (e.g., target temperature of 0 to 10 deg. C. for six hours) could potentially be so large that the concept of a portable isothermal container for a severed finger would be ruled out.

Engineering calculations can give a rough approximation of the amounts of reagents required. Factors that are taken into account include physical properties of the materials such as conductivities, heats of solution and solubilities, heat gain from the surroundings and the initial temperature of the device, i.e., the ambient temperature.

Laboratory experiments were critical in determining the quantities of some of the chemicals used in the test apparatus. The solubility of KSCN was determined experimentally to be approximately 199 g KSCN/100 g water at 6.6 degrees C. (melting point of $C_6H_{12}$). The amount of cyclohexane to be used was determined by adding cyclohexane to a newly mixed saturated solution of KSCN containing octylphenol ethoxylate until the temperature of the system rose to just below 6.6 degrees C. Incidentally, at this point any additional $C_6H_{12}$ added to the system would not freeze although the temperature of the system would remain at approximately 6.6 degrees C. as long as a two phase system persisted. An iterative approach derived from these principles was used in the laboratory to determine the amount of cyclohexane. In summary, the conclusion drawn from the laboratory experiments is that approximately 290 g of cyclohexane is required to thermally buffer 199 g of potassium thiocyanate in 100 g of water contained in an open Dewar flask located in a laboratory at 23 deg. C. The ratio cyclohexane:potassium thiocyanate:water which was thus determined is the same as that used in the test apparatus.

If one assumes an isothermal cooler such as the test apparatus will only be required to operate at a single ambient temperature, for example, room temperature, the optimal design will ensure that the endotherm produced by the reaction is such that the thermal buffer is nearly completely frozen on activation of the device. Subcooling of the frozen material negates the isothermic objective. Incomplete freezing reduces the length of time over which isothermal conditions can be maintained.

In practice, it is almost inevitable that the isothermal cooler will be required to operate over a range of ambient temperatures. For example, an isothermal cooling container for severed limbs could be stored in a factory with an ambient temperature of 15 to 25 degrees Celsius. One important feature of the invention is that it is possible to design a system that can accommodate such a variable ambient temperature. The amount of thermal buffer should be specified so that at the lowest envisioned ambient temperature, i.e., 15 C., the thermal buffer is completely frozen but still at its freezing point. Above the lowest ambient temperature the thermal buffer is thus necessarily not completely frozen. This design will prevent subcooling at low ambient temperatures which is a major deficiency of devices found in the prior art. This feature is especially important for isothermal coolers for severed extremities since subcooling below 0 degrees Celsius will do irreparable damage to the severed extremity.

The above description of the test apparatus relates to the preferred embodiment by way of example only. There are many other examples of embodiments of the invention. For example, Table 2, a non-exhaustive list of salts that might possibly be used instead of KSCN, was arrived at after analysis of data taken from the literature. As will be discussed below, for a variety of reasons KSCN was preferred for the test apparatus. Some of the listed salts may or may not be practicable for the test apparatus.

TABLE 2

| | Potential Salts | | |
|---|---|---|---|
| Salt | ΔH/mole kcal/g-mole | Solubility g/100 mL | Ea kcal/100 mL $H_2O$ |
| Ammonium dichromate | 12.9 | 30.8 | 1.57 |
| Ammonium nitrate | 6.47 | 118.3 | 9.56 |
| Barium perchlorate | 10.5 | 67.3 | 1.81 |
| Cupric nitrate | 10.7 | 45 | 1.62 |
| Lithium nitrate | 7.87 | 34.8 | 2.23 |
| Potassium ferricyanide | 14.3 | 33 | 1.42 |
| Potassium ferrocyanide | 16.5 | 27.8 | 1.08 |
| Potassium nitrate | 8.63 | 13.3 | 1.13 |
| Potassium thiocyanate | 6.08 | 177.2 | 11.16 |
| Potassium pentathionate | 13.14 | 50 | 1.8 |
| Sodium carbonate | 16.22 | 21.5 | 1.22 |
| Sodium chromate | 16.0 | 31.7 | 1.49 |
| Sodium sulfide | 16.65 | 47.5 | 3.28 |
| Sodium sulfite | 11.1 | 32.8 | 1.44 |
| Sodium thiosulfate | 11.3 | 79.4 | 3.65 |
| Strontium nitrate | 12.4 | 60.4 | 2.66 |
| Ammonium bromide | 4.44 | 59.8 | 2.71 |
| Potassium iodide | 5.11 | 127.5 | 3.92 |
| Ammonium sulfate | 2.39 | 70.6 | 1.27 |
| Ammonium thiocyanate | 5.66 | 128 | 9.52 |
| Potassium d-tartrate | 2.84 | 150 | 1.81 |

TABLE 2-continued

| Salt | Potential Salts | | |
|---|---|---|---|
| | ΔH/mole kcal/g-mole | Solubility g/100 mL | Ea kcal/100 mL H$_2$O |
| Sodium iodide | 4.01 | 317.9 | 6.86 |

In compiling the potential salts list, two criteria were to be satisfied: (1) the reaction was to have a large endotherm (ΔH of solution per mole should have a large negative value) (2) the salt was to have a high solubility in water at low temperature in order to produce a large amount of reaction per gram of water added and thus minimize the amount of heat which must be removed from the water in order to reach the target temperature. In other words, a convenient quantity to maximize is the energy absorbed (Ea) for 100 mL of water added, which is the solubility per 100 mL of H$_2$O multiplied by the reaction endotherm per mole of the salt and divided by the molecular weight of the salt. This quantity is tabulated in the right hand column of the potential salts list.

It is clear from a glance at the right hand column of the potential salts list that the salt which should provide the best endotherm is potassium thiocyanate (KSCN, 11.16 kcal/100 mL H$_2$O). The next two salts in order of preference should be ammonium nitrate (NHN$_4$O$_3$, 9.56 kcal/100 mL H$_2$O) and ammonium thiocyanate (NH$_4$SCN, 9.52 kcal/100 mL H$_2$O).

Further calculations can provide a better indicator for choosing potential salts. In order to design a practicable isothermic cooler, it is desirable to take into account the heat that must be removed from the reaction products in order to reach the target temperature. Thus, a better indicator for predicting the best salt would take into account the heat capacity of the reaction products. It is possible to calculate an "Ea available" ("useful endotherm"), i.e., the amount of heat absorption available to withdraw heat from the thermal buffer after the reaction products have been cooled to the target temperature. Maximization of "Ea available" ("useful endotherm") is thus a better criterion for choosing potential salts.

The above calculation can be performed using Kopp's rule for saturated solutions. The amount of heat absorbed in cooling the reaction products will then be the product of the weight of the saturated solution multiplied by the average heat capacity multiplied by the average temperature difference. The above calculation was performed by the inventors for the three preferred salts identified using the data in Table 2. An initial ambient temperature of 20 degrees C. and a target (slush) temperature of 6.6 degrees C. (melting point of cyclohexane) were used in the calculations. The endotherm which would actually be available for cooling the slush liquid and limb is then given in the column entitled "Ea available" (useful endotherm) in the following tabulation of results, Table 3:

TABLE 3

| | Reduction in Available Endotherm | | | |
|---|---|---|---|---|
| Salt | Cp cal/g deg. C. | Weight g/100 mL H$_2$O | ΔH cal | Ea available ("useful endotherm") |
| KSCN | 0.533 | 277.2 | 1,979.8 | 9.18 |
| NH$_4$NO$_3$ | 0.818 | 218.3 | 2,392.8 | 7.17 |
| NH$_4$SCN | 0.833 | 228.0 | 2,545.0 | 6.98 |

The kinetics of the salt reaction are also important. An embodiment of the invention such as the test apparatus requires a rapid process in order to be viable. Potassium thiocyanate (KSCN), ammonium nitrate (NH$_4$NO$_3$) and ammonium thiocyanate (NH$_4$SCN) were experimentally tested. The kinetics were followed by monitoring the temperature under adiabatic conditions (in a vacuum flask bottle) when the salts were added to 100 mL of water. Fortunately, for each salt the final temperature was reached less than 60 seconds after the salt was added.

The use of multiple salts may produce a greater endotherm than simply increasing the amount of reactants (salt and water) in a system such as the one exemplified by the test apparatus. This possibility exists in part because it is known that in some cases a second salt may be more soluble in a solution of a first salt than in pure water (sometimes called the "salting in" effect). In addition, dissolving additional salts into a fixed quantity of water can increase the endotherm with a small increase in the volume of the reactants.

Various binary and ternary combinations of NH$_4$SCN, NH$_4$NO$_3$, KSCN and Na$_2$CO$_3$.10H$_2$O were tested. The procedure followed was to thermostat a saturated solution of one of the three candidate salts in 50 g of water at 6.6 deg. C. with a thermocouple probe in the solution. Different amounts of the second, third and fourth salts were then added. Any instantaneous drop in temperature was recorded as a positive indication of the occurrence of an endothermic reaction. The solubilities of the single salts are shown in Table 4. The results of the combination tests are shown in Table 5.

TABLE 4

| | Solubilities of Single Salts | |
|---|---|---|
| Salt | g/100 mL H$_2$O | g/50 ml H$_2$O |
| KSCN | 199.0 | 99.5 |
| NH$_4$NO$_3$ | 136.3 | 68.2 |
| NH$_4$SCN | 131.5 | 65.8 |
| Na$_2$CO$_3$.H$_2$O | 21.52 | 10.76 |

Note:
The solubilities listed above were determined experimentally at 6.6 deg. C. in 100 mL of H$_2$O except for the value for Na$_2$CO$_3$.10H$_2$O which was taken from a published solubility table.

TABLE 5

| | Binary and Ternary Salt Combinations | | |
|---|---|---|---|
| # | Starting Solution | Salt Added | Endotherm |
| 1 | NH$_4$SCN | NH$_4$NO$_3$ 51 g | yes |
| 2 | NH$_4$SCN + 51 g NH$_4$NO$_3$ | Na$_2$CO$_3$.10H$_2$O 8 g | yes |
| 3 | NH$_4$SCN | Na$_2$CO$_3$.10H$_2$O 25 g | yes |
| 4 | NH$_4$SCN | KSCN 10 g | yes |
| 5 | NH$_4$SCN + 10 g KSCN | Na$_2$CO$_3$.10H$_2$O 129 g | yes |
| 6 | KSCN | NH$_4$NO$_3$ | (did not dissolve) |
| 7 | KSCN + NH$_4$NO$_3$ | NH$_4$SCN 8 g | yes |
| 8 | KSCN + NH$_4$NO$_3$ + 8 g NH$_4$SCN | Na$_2$CO$_3$.10H$_2$O 43 g | yes |
| 9 | KSCN | NH$_4$SCN | (did not dissolve) |
| 10 | KSCN + NH$_4$SCN | Na$_2$CO$_3$.10H$_2$O 50 g | yes |
| 11 | KSCN + NH$_4$SCN + 50 g Na$_2$CO$_3$.10H$_2$O | NH$_4$SCN 5 g | yes |
| 12 | KSCN + NH$_4$SCN + 50 g Na$_2$CO$_3$.10H$_2$O + | KSCN 10 g | yes |

TABLE 5-continued

Binary and Ternary Salt Combinations

| # | Starting Solution | Salt Added | Endotherm |
|---|---|---|---|
| 13 | 5 g NH$_4$SCN KSCN | Na$_2$CO$_3$.10H$_2$O 15 g | yes |
| 14 | KSCN + 15 g Na$_2$CO$_3$.10H$_2$O | NH$_4$SCN 25 g | yes |
| 15 | KSCN + 15 g Na$_2$CO$_3$.10H$_2$O + 25 g NH$_4$SCN | Na$_2$CO$_3$.10H$_2$O 45 g | yes |
| 16 | KSCN | NH$_4$NO$_3$ | no |
| 17 | NH$_4$NO$_3$ | NH$_4$SCN 25 g | yes |
| 18 | NH$_4$NO$_3$ + 25 g NH$_4$SCN | KSCN 5 g | yes |
| 19 | NH$_4$NO$_3$ + 25 g NH$_4$SCN + 5 g KSCN | Na$_2$CO$_3$.10H$_2$O 55 g | yes |
| 20 | NH$_4$NO$_3$ | Na$_2$CO$_3$.10H$_2$O 30 g | yes |
| 21 | NH$_4$NO$_3$ + 30 g Na$_2$CO$_3$.10H$_2$O | NH$_4$SCN 25 g | yes |
| 22 | NH$_4$NO$_3$ | NH$_4$SCN 65 g | yes |
| 23 | NH$_4$NO$_3$ | KSCN | no |

There are many potential thermal buffers. Using data obtained from the literature a number of materials were identified as candidates for a severed extremity cooler with a target temperature between 0 and 10 deg. Celsius. These materials are reported in the following table:

TABLE 6

Candidate Thermal Buffers

| Material | Melting Point deg. C. | ΔH cal/g |
|---|---|---|
| o - dibromobenzene | 1.8 | 12.78 |
| Nitrobenzene | 5.7 | 22.50 |
| Benzene | 5.53 | 30.45 |
| Cyclohexane | 6.6 | 7.47 |
| Antimony pentachloride | 4.0 | 8.0 |
| Phosphorus oxychloride | 1.0 | 20.3 |
| Selenium oxychloride | 9.8 | 6.1 |
| Antimony pentachloride | 4.0 | 8.0 |
| Phosphorus oxychloride | 1.0 | 20.3 |
| Selenium oxychloride | 9.8 | 6.1 |

In the above table note that the melting points are between 0 and 10 degrees Celsius. Note also the relatively high heats of fusion.

There are other considerations in choosing a thermal buffer. For example, the heat capacity of the thermal buffer in the liquid state should be low so that the amount of endotherm used in cooling the thermal buffer to its melting point is minimized. Preferably, the thermal buffer should be nontoxic and inexpensive. The thermal buffer should also be non-reactive with any structural materials or reagents.

People skilled in the field are aware that most surfactants capable of forming oil-in-water emulsions could be used instead of Triton X-100 (octylphenol ethoxylate). Some surfactants may not work because the emulsion is unstable. Others may not work because of interaction with the salts.

It will be appreciated that the above description relates to the preferred embodiment by way of example only. Many variations on the invention will be obvious to those knowledgeable in the field, and such obvious variations are within the scope of the invention as described and claimed, whether or not expressly described.

What is claimed as the invention is:

1. A method for cooling and maintaining an object at a constant temperature, comprising:

adding a salt that dissolves endothermically in water to a mixture containing at least water, a surfactant and an emulsified thermal buffer until a temperature near the freezing point of the thermal buffer has been reached and at least a partial phase change of the thermal buffer has occurred; and bringing the resulting mixture into direct or indirect contact with the object.

2. A method as recited in claim 1 wherein the salt is selected from the group consisting of potassium thiocyanate, ammonium nitrate or ammonium thiocyanate.

3. A method as recited in claim 1 wherein the salt is potassium thiocyanate and the mixture contains water, octylphenol ethoxylate as the surfactant and emulsified cyclohexane as the thermal buffer.

4. A method as recited in claim 1 wherein a plurality of salts are dissolved endothermically into solution.

5. A method as recited in claim 4 wherein the endotherm of the plurality of salts per gram of water is higher than the endotherm of any single salt per gram of water.

6. A method as recited in claim 4 wherein the salts are selected from the group consisting of KSCN, NH$_4$NO$_3$, NH$_4$SCN and Na$_2$CO$_3$.10H$_2$O.

7. A method as recited in claim 6 wherein one of the salts is Na$_2$CO$_3$.10H$_2$O.

8. A device for cooling and maintaining an object at a constant temperature comprising a thermal buffer compartment containing at least a surfactant, an emulsified thermal buffer and water; and a reaction compartment having two portions separated by a frangible barrier, the first portion containing a first reactant and the second portion a second reactant, said first and second reactants reacting endothermically upon contact.

9. A device as recited in claim 8 wherein the first portion of the reaction compartment contains water and the second portion contains a salt that dissolves endothermically into solution.

10. A device for cooling and maintaining an object at constant temperature comprising at least one reaction compartment having two portions separated by a frangible barrier, the first portion containing at least a surfactant, a emulsified thermal buffer and water and the second portion at least one salt that dissolves endothermically into solution.

11. A device as recited in claim 10 further comprising an insulating outer shell.

12. A device as recited in claim 10 wherein the reaction compartment contains a plurality of salts that dissolve endothermically into aqueous solution.

13. A device as recited in claim 10 wherein the reaction compartment is a cooling bag, the surfactant is octylphenol ethoxylate, the thermal buffer is cyclohexane and the salt is potassium thiocyanate.

* * * * *